US008716208B2

(12) United States Patent
Meek et al.

(10) Patent No.: US 8,716,208 B2
(45) **Date of Patent: *May 6, 2014**

(54) COMPOSITION COMPRISING POLYETHYLENE GLYCOL POLYMER AND AMYLASE

(75) Inventors: Michelle Meek, Tyne & Wear (GB); Philip Frank Souter, Northumberland (GB); Neil Joseph Lant, Newcastle upon Tyne (GB); Alan Thomas Brooker, Newcastle upon Tyne (GB); Nigel Patrick Somerville Roberts, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 274 days.

This patent is subject to a terminal disclaimer.

(21) Appl. No.: 13/037,633

(22) Filed: Mar. 1, 2011

(65) Prior Publication Data

US 2011/0212872 A1 Sep. 1, 2011

(30) Foreign Application Priority Data

| | | |
|---|---|---|
| Mar. 1, 2010 | (EP) | 10155094 |
| Mar. 1, 2010 | (EP) | 10155096 |
| Mar. 1, 2010 | (EP) | 10155098 |
| Mar. 1, 2010 | (EP) | 10155100 |
| Apr. 19, 2010 | (EP) | 10160316 |
| Apr. 19, 2010 | (EP) | 10160338 |
| Apr. 19, 2010 | (EP) | 10160344 |
| Apr. 19, 2010 | (EP) | 10160362 |
| Nov. 5, 2010 | (EP) | 10190220 |

(51) Int. Cl.

| | |
|---|---|
| ***C11D 3/386*** | (2006.01) |
| ***C12N 9/28*** | (2006.01) |
| ***C12N 15/00*** | (2006.01) |
| ***C12P 21/04*** | (2006.01) |
| ***C12P 21/06*** | (2006.01) |
| ***C12Q 1/68*** | (2006.01) |
| ***C07H 21/04*** | (2006.01) |

(52) U.S. Cl.
USPC .......... 510/114; 435/202; 435/440; 435/69.1; 435/71.1; 435/6.1; 536/23.2

(58) Field of Classification Search
None
See application file for complete search history.

(56) References Cited

U.S. PATENT DOCUMENTS

| | | | | |
|---|---|---|---|---|
| 5,733,856 | A | 3/1998 | Gopalkrishnan et al. | |
| 2007/0173429 | A1 * | 7/2007 | Souter et al. | 510/314 |
| 2007/0179075 | A1 * | 8/2007 | Souter et al. | 510/320 |
| 2007/0275866 | A1 * | 11/2007 | Dykstra | 510/101 |
| 2008/0193999 | A1 * | 8/2008 | Andersen et al. | 435/201 |
| 2009/0023625 | A1 * | 1/2009 | Tang et al. | 510/320 |
| 2009/0209447 | A1 | 8/2009 | Meek et al. | |

FOREIGN PATENT DOCUMENTS

WO WO2007/138053 A1 12/2007

OTHER PUBLICATIONS

Extended European Search Report and Search Opinion from the European Patent Office, dated Jul. 15, 2011, European Application No. 10190220.3, 7 pages.

* cited by examiner

*Primary Examiner* — Yong Pak
(74) *Attorney, Agent, or Firm* — Melissa G. Krasovec; Steven W. Miller

(57) ABSTRACT

A solid particulate laundry detergent composition including: (a) polyethylene glycol polymer including a polyethylene glycol backbone and polyvinyl acetate side chains, wherein the average molecular weight of the polyethylene glycol backbone is in the range of from 4,000 Da to 8,000 Da, wherein the molecular weight ratio of the polyethylene glycol backbone to the polyvinyl acetate side chains is in the range of from 1:1.2 to 1:2, and wherein the average number of graft sites per ethylene oxide units is in the range of from 0.2 to 0.4; (b) amylase with greater than 90% identity to the AA560 alpha amylase endogenous to *Bacillus* sp. DSM 12649 and including: (i) mutations at one or more of positions 9, 149, 182, 186, 202, 257, 295, 299, 323, 339 and 345; and (ii) mutations at four or more of positions 118, 183, 184, 195, 320 and 458; and (c) laundry detergent ingredients.

12 Claims, No Drawings

COMPOSITION COMPRISING POLYETHYLENE GLYCOL POLYMER AND AMYLASE

FIELD OF THE INVENTION

The present invention relates to a composition comprising polyethylene glycol polymer and amylase enzyme.

BACKGROUND OF THE INVENTION

Consumers of laundry detergent powders continue to desire products with improved cleaning profiles, freshness profiles and dissolution profiles. To meet this consumer demand, laundry detergent powder manufacturers continue to seek optimized laundry detergent powder formulations.

The inventors have found that the whiteness and stain removal profiles of laundry detergent powder are significantly improved by the combination of a specific amylase and specific polyethylene glycol polymer. The inventors have also found that the cleaning profile, freshness profile and/or dissolution profile are further improved by the incorporation of specific bleach technologies such as an oxaziridinium-based bleach catalyst, specific co-bleach particle, and/or specific lipase and/or specific substituted cellulosic polymer into the laundry detergent powder formulation. Further improvements are also observed when some or all of these technologies are incorporated into low-built laundry detergent powder formulations.

SUMMARY OF THE INVENTION

The present invention provides a solid particulate laundry detergent composition comprising:

(a) polyethylene glycol polymer comprising a polyethylene glycol backbone and polyvinyl acetate side chains, wherein the average molecular weight of the polyethylene glycol backbone is in the range of from 4,000 Da to 8,000 Da, wherein the molecular weight ratio of the polyethylene glycol backbone to the polyvinyl acetate side chains is in the range of from 1:1.2 to 1:2, and wherein the average number of graft sites per ethylene oxide units is in the range of from 0.2 to 0.4;

(b) amylase with greater than 90% identity to the AA560 alpha amylase endogenous to *Bacillus* sp. DSM 12649 and comprising:

(i) mutations at one or more of positions 9, 149. 182, 186, 202, 257, 295, 299, 323, 339 and 345; and (ii) mutations at four or more of positions 118, 183, 184, 195, 320 and 458; and (c) laundry detergent ingredients.

DETAILED DESCRIPTION OF THE INVENTION

The solid particulate laundry detergent composition comprises polyethylene glycol polymer, amylase and other laundry detergent ingredients. The polyethylene glycol polymer, amylase and other laundry detergent ingredients are described in more detail below.

Preferably, the composition comprises: (a) anionic detersive surfactant; (b) from 0 wt % to less than 5 wt % zeolite builder; (c) from 0 wt % to less than 5 wt % phosphate builder; and (d) optionally, from 0 wt % to 10 wt % silicate salt. More preferably, the composition comprises (a) anionic detersive surfactant; (b) from 0 wt % to less than 5 wt % zeolite builder; (c) from 0 wt % to less than 5 wt % phosphate builder; and (d) optionally, from 0 wt % to 10 wt % silicate salt/(e) from 5 to 25 wt % sodium carbonate; (f) from 1 wt % to 10 wt % carboxylate polymer; (g) variant of *Thermomyces lanuginosa* lipase having greater than 90% identity with the wild type amino acid and comprising substitution(s) at T231 and/or N233; (h) oxaziridinium-based bleach catalyst having the formula:

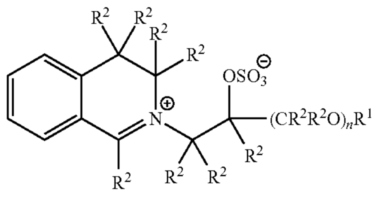

wherein $R^1$ is selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl, and wherein $R^2$ is independently selected from H and methyl groups; and n is an integer from 0 to 1; (i) optionally, co-bleach particle comprising bleach activator, source of hydrogen peroxide and optionally bleach catalyst; and (j) optionally, substituted cellulosic polymer comprising carboxymethyl substituent groups, and having a degree of substitution (DS) of at least 0.55, and having a degree of blockiness (DB) of at least 0.35, and having a DS+DB in the range of from 1.05 to 2.00.

Amylase:

The Amylase typically has greater than 60%, or greater than 70%, or greater than 80%, or greater than 90%, or greater than 95% identity to the AA560 alpha amylase endogenous to *Bacillus* sp. DSM 12649 (shown as SEQ ID NO:1). Preferably, the amylase is a variant of the AA560 alpha amylase endogenous to *Bacillus* sp. Typically, the amylase comprises: (i) mutations at one or more, preferably three or more, or five or more, or seven or more, or ten or more, or even all of positions 9, 149, 182, 186, 202, 257, 295, 299, 323, 339 and 345; and (ii) mutations at four or more, preferably all, of positions 118, 183, 184, 195, 320 and 458. Highly preferably, the amylase comprises all of the mutations: R118K, D183*, G184*, N195F, R320K and R458K.

Preferred variant amylases include those comprising the following sets of mutations:

(i) M9L+M323T;

(ii) M9L+M202L/T/V/I+M323T;

(iii) M9L+N195F+M202L/T/V/I+M323T;

(iv) M9L+R118K+D183*+G184*+R320K+M323T+R458K;

(v) M9L+R118K+D183*+G184*+M202L/T/V/I+R320K+M323T+R458K;

(vi) M9L+G149A+G182T+G186A+M202L+T257I+Y295F+N299Y+M323T+A339S+E345R;

(vii) M9L+G149A+G182T+G186A+M202I+T257I+Y295F+N299Y+M323T+A339S+E345R;

(viii) M9L+R118K+G149A+G182T+D183*+G184*+G186A+M202L+T257I+Y295F+N299Y+R320K+M323T+A339S+E345R+R458K;

(ix) M9L+R118K+G149A+G182T+D183*+G184*+G186A+M202I+T257I+Y295F+N299Y+R320K+M323T+A339S+E345R+R458K;

(x) M9L+R118K+D183*+D184*+N195F+M202L+R320K+M323T+R458K;

(xi) M9L+R118K+D183*+D184*+N195F+M202T+R320K+M323T+R458K;

(xii) M9L+R118K+D183*+D184*+N195F+M202I+R320K+M323T+R458K;

(xiii) M9L+R118K+D183*+D184*+N195F+M202V+R320K+M323T+R458K;

(xiv) M9L+R118K+N150H+D183*+D184*+N195F+M202L+V214T+R320K+M323T+R458K;

(xv) M9L+R118K+D183*+D184*+N195F+M202L+V214T+R320K+M323T+E345N+R458K; or (xvi) M9L+R118K+G149A+G182T+D183*+G184*+G186A+N195F+M202L+T257I+Y295F+N299Y+R320K+M323T+A339S+E345R+R458K A suitable commercially available amylase enzyme includes Stainzyme Plus® (supplied by Novozymes, Bagsvaerd, Denmark).

Polyethylene Glycol Polymer:

The polyethylene glycol polymer comprising a polyethylene glycol backbone and polyvinyl acetate side chains, wherein the average molecular weight of the polyethylene glycol backbone is in the range of from 4,000 Da to 8,000 Da, wherein the molecular weight ratio of the polyethylene glycol backbone to the polyvinyl acetate side chains is in the range of from 1:1.2 to 1:2, and wherein the average number of graft sites per ethylene oxide units is preferably in the range of from 0.2 to 0.4

Solid Particulate Laundry Detergent Composition:

Typically, the composition is a fully formulated laundry detergent composition, not a portion thereof such as a spray-dried or agglomerated particle that only forms part of the laundry detergent composition. However, it is within the scope of the present invention for an additional rinse additive composition (e.g. fabric conditioner or enhancer), or a main wash additive composition (e.g. bleach additive) to also be used in combination with the laundry detergent composition during the method of the present invention. Although, it may be preferred for no bleach additive composition is used in combination with the laundry detergent composition during the method of the present invention.

Typically, the composition comprises a plurality of chemically different particles, such as spray-dried base detergent particles and/or agglomerated base detergent particles and/or extruded base detergent particles, in combination with one or more, typically two or more, or three or more, or four or more, or five or more, or six or more, or even ten or more particles selected from: surfactant particles, including surfactant agglomerates, surfactant extrudates, surfactant needles, surfactant noodles, surfactant flakes; polymer particles such as cellulosic polymer particles, polyester particles, polyamine particles, terephthalate polymer particles, polyethylene glycol polymer particles; builder particles, such as sodium carbonate and sodium silicate co-builder particles, phosphate particles, zeolite particles, silicate salt particles, carbonate salt particles; filler particles such as sulphate salt particles; dye transfer inhibitor particles; dye fixative particles; bleach particles, such as percarbonate particles, especially coated percarbonate particles, such as percarbonate coated with carbonate salt, sulphate salt, silicate salt, borosilicate salt, or any combination thereof, perborate particles, bleach catalyst particles such as transition metal bleach catalyst particles, or oxaziridinium-based bleach catalyst particles, pre-formed peracid particles, especially coated pre-formed peracid particles, and co-bleach particles of bleach activator, source of hydrogen peroxide and optionally bleach catalyst; bleach activator particles such as oxybenzene sulphonate bleach activator particles and tetra acetyl ethylene diamine bleach activator particles; chelant particles such as chelant agglomerates; hueing dye particles; brightener particles; enzyme particles such as protease prills, lipase prills, cellulase prills, amylase prills, mannanase prills, pectate lyase prills, xyloglucanase prills, bleaching enzyme prills, cutinase prills and co-prills of any of these enzymes; clay particles such as montmorillonite particles or particles of clay and silicone; flocculant particles such as polyethylene oxide particles; wax particles such as wax agglomerates; perfume particles such as perfume microcapsules, especially melamine formaldehyde-based perfume microcapsules, starch encapsulated perfume accord particles, and pro-perfume particles such as Schiff base reaction product particles; aesthetic particles such as coloured noodles or needles or lamellae particles, and soap rings including coloured soap rings; and any combination thereof.

Typically, upon dilution in de-ionized water to a concentration of 1 wt % at 20° C., the composition has a pH of above 8.8, or above 8.9, or from 9 to 13, or to 12, or even to 11.

Detergent Ingredients:

The composition typically comprises detergent ingredients. Suitable detergent ingredients include: detersive surfactants including anionic detersive surfactants, non-ionic detersive surfactants, cationic detersive surfactants, zwitterionic detersive surfactants, amphoteric detersive surfactants, and any combination thereof; polymers including carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, and any combination thereof; builders including zeolites, phosphates, citrate, and any combination thereof; buffers and alkalinity sources including carbonate salts and/or silicate salts; fillers including sulphate salts and bio-filler materials; bleach including bleach activators, sources of available oxygen, pre-formed peracids, bleach catalysts, reducing bleach, and any combination thereof; chelants; photobleach; hueing agents; brighteners; enzymes including proteases, amylases, cellulases, lipases, xylogucanases, pectate lyases, mannanases, bleaching enzymes, cutinases, and any combination thereof; fabric softeners including clay, silicones, quaternary ammonium fabric-softening agents, and any combination thereof; flocculants such as polyethylene oxide; perfume including starch encapsulated perfume accords, perfume microcapsules, perfume loaded zeolites, schif base reaction products of ketone perfume raw materials and polyamines, blooming perfumes, and any combination thereof; aesthetics including soap rings, lamellar aesthetic particles, geltin beads, carbonate and/or sulphate salt speckles, coloured clay, and any combination thereof: and any combination thereof.

Detersive Surfactant:

The composition typically comprises detersive surfactant. Suitable detersive surfactants include anionic detersive surfactants, non-ionic detersive surfactant, cationic detersive surfactants, zwitterionic detersive surfactants, amphoteric detersive surfactants, and any combination thereof.

Anionic Detersive Surfactant:

Suitable anionic detersive surfactants include sulphate and sulphonate detersive surfactants.

Suitable sulphonate detersive surfactants include alkyl benzene sulphonate, such as $C_{10-13}$ alkyl benzene sulphonate. Suitable alkyl benzene sulphonate (LAS) is obtainable, or even obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. Another suitable anionic detersive surfactant is alkyl benzene sulphonate that is obtained by DETAL catalyzed process, although other synthesis routes, such as HF, may also be suitable.

Suitable sulphate detersive surfactants include alkyl sulphate, such as $C_{8-18}$ alkyl sulphate, or predominantly $C_{12}$ alkyl sulphate. The alkyl sulphate may be derived from natural sources, such as coco and/or tallow. Alternative, the alkyl sulphate may be derived from synthetic sources such as $C_{12-15}$ alkyl sulphate.

Another suitable sulphate detersive surfactant is alkyl alkoxylated sulphate, such as alkyl ethoxylated sulphate, or a $C_{8-18}$ alkyl alkoxylated sulphate, or a $C_{8-18}$ alkyl ethoxylated sulphate. The alkyl alkoxylated sulphate may have an average degree of alkoxylation of from 0.5 to 20, or from 0.5 to 10. The alkyl alkoxylated sulphate may be a $C_{8-18}$ alkyl ethoxylated sulphate, typically having an average degree of ethoxylation of from 0.5 to 10, or from 0.5 to 7, or from 0.5 to 5 or from 0.5 to 3.

The alkyl sulphate, alkyl alkoxylated sulphate and alkyl benzene sulphonates may be linear or branched, substituted or un-substituted.

The anionic detersive surfactant may be a mid-chain branched anionic detersive surfactant, such as a mid-chain branched alkyl sulphate and/or a mid-chain branched alkyl benzene sulphonate. The mid-chain branches are typically $C_{1-4}$ alkyl groups, such as methyl and/or ethyl groups.

Another suitable anionic detersive surfactant is alkyl ethoxy carboxylate.

The anionic detersive surfactants are typically present in their salt form, typically being complexed with a suitable cation. Suitable counter-ions include $Na^+$ and $K^+$, substituted ammonium such as $C_1$-$C_6$ alkanolammonium such as mono-ethanolamine (MEA) tri-ethanolamine (TEA), di-ethanolamine (DEA), and any mixture thereof.

Non-Ionic Detersive Surfactant:

Suitable non-ionic detersive surfactants are selected from the group consisting of: $C_8$-$C_{18}$ alkyl ethoxylates, such as, NEODOL® non-ionic surfactants from Shell; $C_6$-$C_{12}$ alkyl phenol alkoxylates wherein optionally the alkoxylate units are ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, such as alkylpolyglycosides; polyhydroxy fatty acid amides; ether capped poly(oxyalkylated) alcohol surfactants; and mixtures thereof.

Suitable non-ionic detersive surfactants are alkyl polyglucoside and/or an alkyl alkoxylated alcohol.

Suitable non-ionic detersive surfactants include alkyl alkoxylated alcohols, such as $C_{8-18}$ alkyl alkoxylated alcohol, or a $C_{8-18}$ alkyl ethoxylated alcohol. The alkyl alkoxylated alcohol may have an average degree of alkoxylation of from 0.5 to 50, or from 1 to 30, or from 1 to 20, or from 1 to 10. The alkyl alkoxylated alcohol may be a $C_{8-18}$ alkyl ethoxylated alcohol, typically having an average degree of ethoxylation of from 1 to 10, or from 1 to 7, or from 1 to 5, or from 3 to 7. The alkyl alkoxylated alcohol can be linear or branched, and substituted or un-substituted.

Suitable nonionic detersive surfactants include secondary alcohol-based detersive surfactants having the formula:

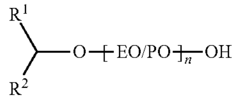

wherein $R^1$=linear or branched, substituted or unsubstituted, saturated or unsaturated $C_{2-8}$ alkyl;

wherein $R^2$=linear or branched, substituted or unsubstituted, saturated or unsaturated $C_{2-8}$ alkyl, wherein the total number of carbon atoms present in $R^1$+$R^2$ moieties is in the range of from 7 to 13;

wherein EO/PO are alkoxy moieties selected from ethoxy, propoxy, or mixtures thereof, optionally the EO/PO alkoxyl moieties are in random or block configuration;

wherein n is the average degree of alkoxylation and is in the range of from 4 to 10.

Other suitable non-ionic detersive surfactants include EO/PO block co-polymer surfactants, such as the Plurafac® series of surfactants available from BASF, and sugar-derived surfactants such as alkyl N-methyl glucose amide.

Cationic Detersive Surfactant:

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

$$(R)(R_1)(R_2)(R_3)N^+X^-$$

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, such as chloride; sulphate; and sulphonate. Suitable cationic detersive surfactants are mono-$C_{6-18}$ alkyl mono-hydroxyethyl di-methyl quaternary ammonium chlorides. Suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Zwitterionic and/or Amphoteric Detersive Surfactant:

Suitable zwitterionic and/or amphoteric detersive surfactants include amine oxide such as dodecyldimethylamine N-oxide, alkanolamine sulphobetaines, coco-amidopropyl betaines, $HN^-$—R—$CO_2^-$ based surfactants, wherein R can be any bridging group, such as alkyl, alkoxy, aryl or amino acids.

Polymer:

Suitable polymers include carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, and any combination thereof.

Carboxylate Polymer:

Suitable carboxylate polymers include maleate/acrylate random copolymer or polyacrylate homopolymer. The carboxylate polymer may be a polyacrylate homopolymer having a molecular weight of from 4,000 Da to 9,000 Da, or from 6,000 Da to 9,000 Da. Other suitable carboxylate polymers are co-polymers of maleic acid and acrylic acid, and may have a molecular weight in the range of from 4,000 Da to 90,000 Da.

Polyethylene Glycol Polymer:

Suitable polyethylene glycol polymers include random graft co-polymers comprising: (i) hydrophilic backbone comprising polyethylene glycol; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22.

Polyester Soil Release Polymers:

Suitable polyester soil release polymers have a structure as defined by one of the following structures (I), (II) or (III):

$$—[(OCHR^1—CHR^2)_a—O—OC—Ar—CO—]_d \quad (I)$$

$$—[(OCHR^3—CHR^4)_b—O—OC\text{-}sAr—CO—]_e \quad (II)$$

$$—[(OCHR^5—CHR^6)_c—OR^7]_f \quad (III)$$

wherein:

a, b and c are from 1 to 200;

d, e and f are from 1 to 50;

Ar is a 1,4-substituted phenylene;

sAr is 1,3-substituted phenylene substituted in position 5 with $SO_3Me$;

Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or any mixture thereof;

$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group. Suitable polyester soil release polymers are terephthalate polymers having the structure of formula (I) or (II) above.

Suitable polyester soil release polymers include the Repel-o-tex series of polymers such as Repel-o-tex SF2 (Rhodia) and/or the Texcare series of polymers such as Texcare SRA300 (Clariant).

Amine Polymer:

Suitable amine polymers include polyethylene imine polymers, such as alkoxylated polyalkyleneimines, optionally comprising a polyethylene and/or polypropylene oxide block.

Cellulosic Polymer:

The composition can comprise cellulosic polymers, such as polymers selected from alkyl cellulose, alkyl alkoxyalkyl cellulose, carboxyalkyl cellulose, alkyl carboxyalkyl, and any combination thereof. Suitable cellulosic polymers are selected from carboxymethyl cellulose, methyl cellulose, methyl hydroxyethyl cellulose, methyl carboxymethyl cellulose, and mixtures thereof. The carboxymethyl cellulose can have a degree of carboxymethyl substitution from 0.5 to 0.9 and a molecular weight from 100,000 Da to 300,000 Da. Another suitable cellulosic polymer is hydrophobically modified carboxymethyl cellulose, such as Finnfix SH-1 (CP Kelco).

Other suitable cellulosic polymers may have a degree of substitution (DS) of from 0.01 to 0.99 and a degree of blockiness (DB) such that either DS+DB is of at least 1.00 or $DB+2DS-DS^2$ is at least 1.20. The substituted cellulosic polymer can have a degree of substitution (DS) of at least 0.55. The substituted cellulosic polymer can have a degree of blockiness (DB) of at least 0.35. The substituted cellulosic polymer can have a DS+DB, of from 1.05 to 2.00. A suitable substituted cellulosic polymer is carboxymethylcellulose.

Another suitable cellulosic polymer is cationically modified hydroxyethyl cellulose.

Dye Transfer Inhibitor Polymer:

Suitable dye transfer inhibitor (DTI) polymers include polyvinyl pyrrolidone (PVP), vinyl co-polymers of pyrrolidone and imidazoline (PVPVI), polyvinyl N-oxide (PVNO), and any mixture thereof.

Hexamethylenediamine Derivative Polymers:

Suitable polymers include hexamethylenediamine derivative polymers, typically having the formula:

$$R_2(CH_3)N^+(CH_2)6N^+(CH_3)R_2.2X^-$$

wherein $X^-$ is a suitable counter-ion, for example chloride, and R is a poly(ethylene glycol) chain having an average degree of ethoxylation of from 20 to 30. Optionally, the poly(ethylene glycol) chains may be independently capped with sulphate and/or sulphonate groups, typically with the charge being balanced by reducing the number of $X^-$ counter-ions, or (in cases where the average degree of sulphation per molecule is greater than two), introduction of $Y^+$ counter-ions, for example sodium cations.

Builder:

Suitable builders include zeolites, phosphates, citrates, and any combination thereof.

Zeolite Builder:

The composition typically comprises from 0 wt % to 10 wt %, zeolite builder, or to 8 wt %, or to 6 wt %, or to 4 wt %, or to 3 wt %, or to 2 wt %, or even to 1 wt % zeolite builder. The composition may even be substantially free of zeolite builder; substantially free means "no deliberately added". Typical zeolite builders include zeolite A, zeolite P, zeolite MAP, zeolite X and zeolite Y.

Phosphate Builder:

The composition typically comprises from 0 wt % to 10 wt % phosphate builder, or to 8 wt %, or to 6 wt %, or to 4 wt %, or to 3 wt %, or to 2 wt %, or even to 1 wt % phosphate builder. The composition may even be substantially free of phosphate builder; substantially free means "no deliberately added". A typical phosphate builder is sodium tri-polyphosphate (STPP).

Citrate:

A suitable citrate is sodium citrate. However, citric acid may also be incorporated into the composition, which can form citrate in the wash liquor.

Buffer and Alkalinity Source:

Suitable buffers and alkalinity sources include carbonate salts and/or silicate salts and/or double salts such as burkeitte.

Carbonate Salt:

A suitable carbonate salt is sodium carbonate and/or sodium bicarbonate. The composition may comprise bicarbonate salt. It may be suitable for the composition to comprise low levels of carbonate salt, for example, it may be suitable for the composition to comprise from 0 wt % to 10 wt % carbonate salt, or to 8 wt %, or to 6 wt %, or to 4 wt %, or to 3 wt %, or to 2 wt %, or even to 1 wt % carbonate salt. The composition may even be substantially free of carbonate salt; substantially free means "no deliberately added".

The carbonate salt may have a weight average mean particle size of from 100 to 500 micrometers. Alternatively, the carbonate salt may have a weight average mean particle size of from 10 to 25 micrometers.

Silicate Salt:

The composition may comprise from 0 wt % to 20 wt % silicate salt, or to 15 wt %, or to 10 wt %, or to 5 wt %, or to 4 wt %, or even to 2 wt %, and may comprise from above 0 wt %, or from 0.5 wt %, or even from 1 wt % silicate salt. The silicate can be crystalline or amorphous. Suitable crystalline silicates include crystalline layered silicate, such as SKS-6. Other suitable silicates include 1.6R silicate and/or 2.0R silicate. A suitable silicate salt is sodium silicate. Another suitable silicate salt is sodium metasilicate.

Filler:

The composition may comprise from 0 wt % to 70% filler. Suitable fillers include sulphate salts and/or bio-filler materials.

Sulphate Salt:

A suitable sulphate salt is sodium sulphate. The sulphate salt may have a weight average mean particle size of from 100 to 500 micrometers, alternatively, the sulphate salt may have a weight average mean particle size of from 10 to 45 micrometers.

Bio-Filler Material:

A suitable bio-filler material is alkali and/or bleach treated agricultural waste.

Bleach:

The composition may comprise bleach. Alternatively, the composition may be substantially free of bleach; substantially free means "no deliberately added". Suitable bleach includes bleach activators, sources of available oxygen, pre-formed peracids, bleach catalysts, reducing bleach, and any combination thereof. If present, the bleach, or any component thereof, for example the pre-formed peracid, may be coated, such as encapsulated, or clathrated, such as with urea or cyclodextrin.

Bleach Activator:

Suitable bleach activators include: tetraacetylethylenediamine (TAED); oxybenzene sulphonates such as nonanoyl oxybenzene sulphonate (NOBS), caprylamidononanoyl oxybenzene sulphonate (NACA-OBS), 3,5,5-trimethyl hexanoyloxybenzene sulphonate (Iso-NOBS), dodecyl oxybenzene sulphonate (LOBS), and any mixture thereof; caprolactams; pentaacetate glucose (PAG); nitrile quaternary ammonium; imide bleach activators, such as N-nonanoyl-N-methyl acetamide; and any mixture thereof.

Source of Available Oxygen:

A suitable source of available oxygen (AvOx) is a source of hydrogen peroxide, such as percarbonate salts and/or perborate salts, such as sodium percarbonate. The source of peroxygen may be at least partially coated, or even completely coated, by a coating ingredient such as a carbonate salt, a sulphate salt, a silicate salt, borosilicate, or any mixture thereof, including mixed salts thereof. Suitable percarbonate salts can be prepared by a fluid bed process or by a crystallization process. Suitable perborate salts include sodium perborate mono-hydrate (PB1), sodium perborate tetra-hydrate (PB4), and anhydrous sodium perborate which is also known as fizzing sodium perborate. Other suitable sources of AvOx include persulphate, such as oxone. Another suitable source of AvOx is hydrogen peroxide.

Pre-Formed Peracid:

A suitable pre-formed peracid is N,N-pthaloylamino peroxycaproic acid (PAP).

Bleach Catalyst:

Suitable bleach catalysts include oxaziridinium-based bleach catalysts, transition metal bleach catalysts and bleaching enzymes.

Oxaziridinium-Based Bleach Catalyst:

A suitable oxaziridinium-based bleach catalyst has the formula:

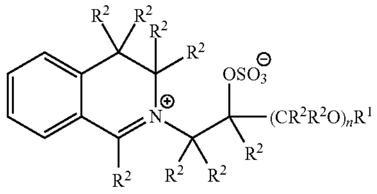

wherein: $R^1$ is selected from the group consisting of: H, a branched alkyl group containing from 3 to 24 carbons, and a linear alkyl group containing from 1 to 24 carbons; $R^1$ can be a branched alkyl group comprising from 6 to 18 carbons, or a linear alkyl group comprising from 5 to 18 carbons, $R^1$ can be selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl; $R^2$ is independently selected from the group consisting of: H, a branched alkyl group comprising from 3 to 12 carbons, and a linear alkyl group comprising from 1 to 12 carbons; optionally $R^2$ is independently selected from H and methyl groups; and n is an integer from 0 to 1.

Transition Metal Bleach Catalyst:

The composition may include transition metal bleach catalyst, typically comprising copper, iron, titanium, ruthenium, tungsten, molybdenum, and/or manganese cations. Suitable transition metal bleach catalysts are manganese-based transition metal bleach catalysts.

Reducing Bleach:

The composition may comprise a reducing bleach. However, the composition may be substantially free of reducing bleach; substantially free means "no deliberately added". Suitable reducing bleach include sodium sulphite and/or thiourea dioxide (TDO).

Co-Bleach Particle:

The composition may comprise a co-bleach particle. Typically, the co-bleach particle comprises a bleach activator and a source of peroxide. It may be highly suitable for a large amount of bleach activator relative to the source of hydrogen peroxide to be present in the co-bleach particle. The weight ratio of bleach activator to source of hydrogen peroxide present in the co-bleach particle can be at least 0.3:1, or at least 0.6:1, or at least 0.7:1, or at least 0.8:1, or at least 0.9:1, or at least 1.0:1.0, or even at least 1.2:1 or higher.

The co-bleach particle can comprise: (i) bleach activator, such as TAED; and (ii) a source of hydrogen peroxide, such as sodium percarbonate. The bleach activator may at least partially, or even completely, enclose the source of hydrogen peroxide.

The co-bleach particle may comprise a binder. Suitable binders are carboxylate polymers such as polyacrylate polymers, and/or surfactants including non-ionic detersive surfactants and/or anionic detersive surfactants such as linear $C_{11}$-$C_{13}$ alkyl benzene sulphonate.

The co-bleach particle may comprise bleach catalyst, such as an oxaziridium-based bleach catalyst.

Chelant:

Suitable chelants are selected from: diethylene triamine pentaacetate, diethylene triamine penta(methyl phosphonic acid), ethylene diamine-N'N'-disuccinic acid, ethylene diamine tetraacetate, ethylene diamine tetra(methylene phosphonic acid), hydroxyethane di(methylene phosphonic acid), and any combination thereof. A suitable chelant is ethylene diamine-N'N'-disuccinic acid (EDDS) and/or hydroxyethane diphosphonic acid (HEDP). The laundry detergent composition may comprise ethylene diamine-N'N'-disuccinic acid or salt thereof. The ethylene diamine-N'N'-disuccinic acid may be in S,S enantiomeric form. The composition may comprise 4,5-dihydroxy-m-benzenedisulfonic acid disodium salt. Suitable chelants may also be calcium crystal growth inhibitors.

Calcium Carbonate Crystal Growth Inhibitor:

The composition may comprise a calcium carbonate crystal growth inhibitor, such as one selected from the group consisting of: 1-hydroxyethanediphosphonic acid (HEDP) and salts thereof; N,N-dicarboxymethyl-2-aminopentane-1,5-dioic acid and salts thereof; 2-phosphonobutane-1,2,4-tricarboxylic acid and salts thereof; and any combination thereof.

Photobleach:

Suitable photobleaches are zinc and/or aluminium sulphonated phthalocyanines.

Hueing Agent:

The hueing agent (also defined herein as hueing dye) is typically formulated to deposit onto fabrics from the wash liquor so as to improve fabric whiteness perception. The hueing agent is typically blue or violet. It may be suitable that the hueing dye(s) have a peak absorption wavelength of from 550 nm to 650 nm, or from 570 nm to 630 nm. The hueing agent may be a combination of dyes which together have the visual effect on the human eye as a single dye having a peak absorption wavelength on polyester of from 550 nm to 650 nm, or from 570 nm to 630 nm. This may be provided for example by mixing a red and green-blue dye to yield a blue or violet shade.

Dyes are typically coloured organic molecules which are soluble in aqueous media that contain surfactants. Dyes maybe selected from the classes of basic, acid, hydrophobic, direct and polymeric dyes, and dye-conjugates. Suitable polymeric hueing dyes are commercially available, for example from Milliken, Spartanburg, S.C., USA.

Examples of suitable dyes are violet DD, direct violet 7, direct violet 9, direct violet 11, direct violet 26, direct violet 31, direct violet 35, direct violet 40, direct violet 41, direct violet 51, direct violet 66, direct violet 99, acid violet 50, acid blue 9, acid violet 17, acid black 1, acid red 17, acid blue 29, solvent violet 13, disperse violet 27 disperse violet 26, disperse violet 28, disperse violet 63 and disperse violet 77, basic blue 16, basic blue 65, basic blue 66, basic blue 67, basic blue 71, basic blue 159, basic violet 19, basic violet 35, basic violet 38, basic violet 48; basic blue 3, basic blue 75, basic blue 95, basic blue 122, basic blue 124, basic blue 141, thiazolium dyes, reactive blue 19, reactive blue 163, reactive blue 182, reactive blue 96, Liquitint® Violet CT (Milliken, Spartanburg, USA) and Azo-CM-Cellulose (Megazyme, Bray, Republic of Ireland). Other suitable hueing agents are hueing dye-photobleach conjugates, such as the conjugate of sulphonated zinc phthalocyanine with direct violet 99. A particularly suitable hueing agent is a combination of acid red 52 and acid blue 80, or the combination of direct violet 9 and solvent violet 13.

Brightener:

Suitable brighteners are stilbenes, such as brightener 15. Other suitable brighteners are hydrophobic brighteners, and brightener 49. The brightener may be in micronized particulate form, having a weight average particle size in the range of from 3 to 30 micrometers, or from 3 micrometers to 20 micrometers, or from 3 to 10 micrometers. The brightener can be alpha or beta crystalline form.

Enzyme:

Suitable enzymes include proteases, amylases, cellulases, lipases, xylogucanases, pectate lyases, mannanases, bleaching enzymes, cutinases, and mixtures thereof.

For the enzymes, accession numbers and IDs shown in parentheses refer to the entry numbers in the databases Genbank, EMBL and/or Swiss-Prot. For any mutations, standard 1-letter amino acid codes are used with a * representing a deletion. Accession numbers prefixed with DSM refer to micro-organisms deposited at Deutsche Sammlung von Mikroorganismen and Zellkulturen GmbH, Mascheroder Weg 1b, 38124 Brunswick (DSMZ).

Protease.

The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, Bacillus alkalophilus* (P27963, ELYA_BACAO), *Bacillus subtilis, Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the *Fusarium* protease and the chymotrypsin proteases derived from *Cellumonas* (A2RQE2).

(c) metalloproteases, including those derived from *Bacillus amyloliquefaciens* (P06832, NPRE_BACAM).

Suitable proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International; those sold under the tradename Opticlean® and Optimase® by Solvay Enzymes; those available from Henkel/Kemira, namely BLAP (P29599 having the following mutations S99D+S101 R+S103A+V104I+G159S), and variants thereof including BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D) all from Henkel/Kemira; and KAP (*Bacillus alkalophilus* subtilisin with mutations A230V+S256G+S259N) from Kao.

Other Amylase:

Suitable other amylases are alpha-amylases, including those of bacterial or fungal origin. Chemically or genetically modified mutants (variants) are included. A suitable alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Suitable amylases include:

(a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

(b) AA560 amylase (CBU30457, HD066534) and variants thereof, especially the variants with one or more substitutions in the following positions: 26, 30, 33, 82, 37, 106, 118, 128, 133, 150, 160, 178, 193, 203, 214, 231, 256, 258, 269, 270, 272, 283, 296, 298, 299, 303, 304, 305, 311, 314, 315, 318, 319, 361, 378, 383, 419, 421, 437, 441, 444, 445, 446, 447, 450, 461, 471, 482, 484, optionally that also contain the deletions of D183* and G184*.

(c) variants exhibiting at least 90% identity with the wild-type enzyme from *Bacillus* SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase®, Purastar®, Optisize HT Plus®, Enzysize®, Powerase® and Purastar Oxam®, Maxamyl® (Genencor International Inc.) and KAM® (KAO, Japan). Suitable amylases are Natalase® and Stainzyme®.

Cellulase:

The composition may comprise a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum.*

Commercially available cellulases include Celluzyme®, and Carezyme® (Novozymes A/S), Clazinase®, and Puradax HA® (Genencor International Inc.), and KAC-500(B)® (Kao Corporation).

The cellulase can include microbial-derived endoglucanases exhibiting endo-beta-1,4-glucanase activity (E.C. 3.2.1.4), including a bacterial polypeptide endogenous to a member of the genus *Bacillus* sp. AA349 and mixtures thereof. Suitable endoglucanases are sold under the tradenames Celluclean® and Whitezyme® (Novozymes A/S, Bagsvaerd, Denmark).

The composition may comprise a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Suitable cellulases may also exhibit xyloglucanase activity, such as Whitezyme®.

Lipase.

The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*), or from *H. insolens*, a *Pseudomonas lipase*, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus.*

The lipase may be a "first cycle lipase", optionally a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Suitable lipases would include those sold under the tradenames Lipex®, Lipolex® and Lipoclean® by Novozymes, Bagsvaerd, Denmark.

The composition may comprise a variant of *Thermomyces lanuginosa* (O59952) lipase having >90% identity with the wild type amino acid and comprising substitution(s) at T231 and/or N233, optionally T231R and/or N233R.

Xyloglucanase:

Suitable xyloglucanase enzymes may have enzymatic activity towards both xyloglucan and amorphous cellulose substrates. The enzyme may be a glycosyl hydrolase (GH) selected from GH families 5, 12, 44 or 74. The glycosyl hydrolase selected from GH family 44 is particularly suitable. Suitable glycosyl hydrolases from GH family 44 are the XYG1006 glycosyl hydrolase from *Paenibacillus polyxyma* (ATCC 832) and variants thereof.

Pectate Lyase:

Suitable pectate lyases are either wild-types or variants of *Bacillus*-derived pectate lyases (CAF05441, AAU25568) sold under the tradenames Pectawash®, Pectaway® and X-Pect® (from Novozymes A/S, Bagsvaerd, Denmark).

Mannanase:

Suitable mannanases are sold under the tradenames Mannaway® (from Novozymes A/S, Bagsvaerd, Denmark), and Purabrite® (Genencor International Inc., Palo Alto, Calif.).

Bleaching Enzyme:

Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. It may be advantageous for additional organic compounds, especially aromatic compounds, to be incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the *Mycobacterium smegmatis* perhydrolase, variants of so-called CE-7 perhydrolases, and variants of wild-type subtilisin Carlsberg possessing perhydrolase activity.

Cutinase:

Suitable cutinases are defined by E.C. Class 3.1.1.73, optionally displaying at least 90%, or 95%, or most optionally at least 98% identity with a wild-type derived from one of *Fusarium solani, Pseudomonas Mendocina* or *Humicola Insolens.*

Identity.

The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

Fabric-Softener:

Suitable fabric-softening agents include clay, silicone and/or quaternary ammonium compounds. Suitable clays include montmorillonite clay, hectorite clay and/or laponite clay. A suitable clay is montmorillonite clay. Suitable silicones include amino-silicones and/or polydimethylsiloxane (PDMS). A suitable fabric softener is a particle comprising clay and silicone, such as a particle comprising montmorillonite clay and PDMS.

Flocculant:

Suitable flocculants include polyethylene oxide; for example having an average molecular weight of from 300,000 Da to 900,000 Da.

Suds Suppressor:

Suitable suds suppressors include silicone and/or fatty acid such as stearic acid.

Perfume:

Suitable perfumes include perfume microcapsules, polymer assisted perfume delivery systems including Schiff base perfume/polymer complexes, starch-encapsulated perfume accords, perfume-loaded zeolites, blooming perfume accords, and any combination thereof. A suitable perfume microcapsule is melamine formaldehyde based, typically comprising perfume that is encapsulated by a shell comprising melamine formaldehyde. It may be highly suitable for such perfume microcapsules to comprise cationic and/or cationic precursor material in the shell, such as polyvinyl formamide (PVF) and/or cationically modified hydroxyethyl cellulose (catHEC).

Aesthetic:

Suitable aesthetic particles include soap rings, lamellar aesthetic particles, geltin beads, carbonate and/or sulphate salt speckles, coloured clay particles, and any combination thereof.

Method of Laundering Fabric:

The method of laundering fabric typically comprises the step of contacting the composition to water to form a wash liquor, and laundering fabric in said wash liquor, wherein typically the wash liquor has a temperature of above 0° C. to 90° C., or to 60° C., or to 40° C., or to 30° C., or to 20° C., or to 10° C., or even to 8° C. The fabric may be contacted to the water prior to, or after, or simultaneous with, contacting the laundry detergent composition with water. The composition can be used in pre-treatment applications.

Typically, the wash liquor is formed by contacting the laundry detergent to water in such an amount so that the concentration of laundry detergent composition in the wash liquor is from above 0 g/l to 5 g/l, or from 1 g/l, and to 4.5 g/l, or to 4.0 g/l, or to 3.5 g/l, or to 3.0 g/l, or to 2.5 g/l, or even to 2.0 g/l, or even to 1.5 g/l.

The method of laundering fabric may be carried out in a top-loading or front-loading automatic washing machine, or can be used in a hand-wash laundry application. In these applications, the wash liquor formed and concentration of laundry detergent composition in the wash liquor is that of the main wash cycle. Any input of water during any optional rinsing step(s) is not included when determining the volume of the wash liquor.

The wash liquor may comprise 40 liters or less of water, or 30 liters or less, or 20 liters or less, or 10 liters or less, or 8 liters or less, or even 6 liters or less of water. The wash liquor may comprise from above 0 to 15 liters, or from 2 liters, and to 12 liters, or even to 8 liters of water.

Typically from 0.01 kg to 2 kg of fabric per liter of wash liquor is dosed into said wash liquor. Typically from 0.01 kg, or from 0.05 kg, or from 0.07 kg, or from 0.10 kg, or from 0.15 kg, or from 0.20 kg, or from 0.25 kg fabric per liter of wash liquor is dosed into said wash liquor.

Optionally, 50 g or less, or 45 g or less, or 40 g or less, or 35 g or less, or 30 g or less, or 25 g or less, or 20 g or less, or even 15 g or less, or even 10 g or less of the composition is contacted to water to form the wash liquor.

EXAMPLES

| Ingredient | Amount |
|---|---|
| Polyethylene glycol polymer (comprising a polyethylene glycol backbone and polyvinyl acetate side chains, wherein the average molecular weight of the polyethylene glycol backbone is in the range of from 4,000 Da to 8,000 Da, wherein the molecular weight ratio of the polyethylene glycol backbone to the polyvinyl acetate side chains is in the range of from 1:1.2 to 1:2, and wherein the average number of graft sites per ethylene oxide units is preferably in the range of from 0.2 to 0.4) | from 0.5 wt % to 1.5 wt % |
| Amylase (Stainzyme Plus, having an enzyme activity of 14 mg active enzyme/g) | from 0.1 wt % to 0.5 wt % |
| Anionic detersive surfactant (such as alkyl benzene sulphonate, alkyl ethoxylated sulphate and mixtures thereof) | from 8 wt % to 15 wt % |
| Non-ionic detersive surfactant (such as alkyl ethoxylated alcohol) | from 0.5 wt % to 4 wt % |
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 wt % to 4 wt % |
| Carboxylate polymer (such as co-polymers of maleic acid and acrylic acid) | from 1 wt % to 4 wt % |
| Polyethylene glycol polymer (such as a polyethylene glycol polymer comprising poly vinyl acetate side chains) | from 0 wt % to 4 wt % |

-continued

| Ingredient | Amount |
|---|---|
| Polyester soil release polymer (such as Repel-o-tex and/or Texcare polymers) | from 0.1 to 2 wt % |
| Cellulosic polymer (such as carboxymethyl cellulose, methyl cellulose and combinations thereof) | from 0.5 wt % to 2 wt % |
| Other polymer (such as amine polymers, dye transfer inhibitor polymers, hexamethylenediamine derivative polymers, and mixtures thereof) | from 0 wt % to 4 wt % |
| Zeolite builder and phosphate builder (such as zeolite 4A and/or sodium tripolyphosphate) | from 0 wt % to 4 wt % |
| Other builder (such as sodium citrate and/or citric acid) | from 0 wt % to 3 wt % |
| Carbonate salt (such as sodium carbonate and/or sodium bicarbonate) | from 15 wt % to 30 wt % |
| Silicate salt (such as sodium silicate) | from 0 wt % to 10 wt % |
| Filler (such as sodium sulphate and/or bio-fillers) | from 10 wt % to 40 wt % |
| Source of available oxygen (such as sodium percarbonate) | from 10 wt % to 20 wt % |
| Bleach activator (such as tetraacetylethylene diamine (TAED) and/or nonanoyloxybenzenesulphonate (NOBS) | from 2 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre-formed peracid) | from 0 wt % to 10 wt % |
| Chelant (such as ethylenediamine-N'N'-disuccinic acid (EDDS) and/or hydroxyethane diphosphonic acid (HEDP) | from 0.2 wt % to 1 wt % |
| Photobleach (such as zinc and/or aluminium sulphonated phthalocyanine) | from 0 wt % to 0.1 wt % |
| Hueing agent (such as direct violet 99, acid red 52, acid blue 80, direct violet 9, solvent violet 13 and any combination thereof) | from 0 wt % to 0.5 wt % |
| Brightener (such as brightener 15 and/or brightener 49) | from 0.1 wt % to 0.4 wt % |
| Protease (such as Savinase, Polarzyme, Purafect, FN3, FN4 and any combination thereof), typically having an enzyme activity of from 20 to 100 mg active enzyme/g | from 0.1 wt % to 1.5 wt % |
| Amylase (such as Termamyl, Termamyl Ultra, Natalase, Optisize HT Plus, Powerase, Stainzyme and any combination thereof), typically having an enzyme activity of from 10 to 50 mg active enzyme/g | from 0.05 wt % to 0.2 wt % |
| Cellulase (such as Carezyme, Celluzyme and/or Celluclean), typically having an enzyme activity of from 10 to 50 mg active enzyme/g | from 0.05 wt % to 0.5 wt % |
| Lipase (such as Lipex, Lipolex, Lipoclean and any combination thereof), typically having an enzyme activity of from 10 to 50 mg active enzyme/g | from 0.2 to 1 wt % |
| Other enzyme (such as xyloglucanase (e.g. Whitezyme), cutinase, pectate lyase, mannanase, bleaching enzyme), typically having an enzyme activity of from 10 to 50 mg active enzyme/g | from 0 wt % to 2 wt % |
| Fabric softener (such as montmorillonite clay and/or polydimethylsiloxane (PDMS) | from 0 wt % to 15 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | Balance |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm”.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid particulate laundry detergent composition comprising:

(a) polyethylene glycol polymer comprising a polyethylene glycol backbone and polyvinyl acetate side chains, wherein the average molecular weight of the polyethylene glycol backbone is in the range of from 4,000 Da to 8,000 Da, wherein the molecular weight ratio of the polyethylene glycol backbone to the polyvinyl acetate side chains is in the range of from 1:1.2 to 1:2, and wherein the average number of graft sites per ethylene oxide units is in the range of from 0.2 to 0.4;

(b) amylase with greater than 90% identity to the AA560 alpha amylase endogenous to *Bacillus* sp. DSM 12649 having sequence ID NO:1 and comprising:

(i) mutations at one or more of positions 9, 149. 182, 186, 202, 257, 295, 299, 323, 339 and 345; and (ii) mutations at four or more of positions 118, 183, 184, 195, 320 and 458; and (c) laundry detergent ingredients.

2. A composition according to claim 1, wherein upon dilution in de-ionized water to a concentration of 1 wt % at 20° C., the composition has a pH of from 9 to 13.

3. A composition according to claim 1, wherein the amylase comprises mutations at the following positions: R118K, D183*, G184*, N195F, R320K and R458K.

4. A composition according to claim 1, wherein the composition comprises:

(a) anionic detersive surfactant;

(b) from 0 wt % to less than 5 wt % zeolite builder;

(c) from 0 wt % to less than 5 wt % phosphate builder; and (d) optionally, from 0 wt % to 10 wt % silicate salt.

5. A composition according to claim 1, wherein the composition comprises XYG1006 glycosyl hydrolase from *Paenibacillus polyxyma* and variants thereof.

6. A composition according to claim 1, wherein the composition comprises co-bleach particle comprising a bleach activator, a source of hydrogen peroxide and optionally a bleach catalyst.

7. A composition according to claim 1, wherein the composition comprises oxaziridinium-based bleach catalyst having the formula:

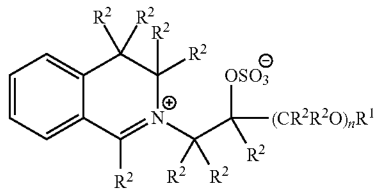

wherein $R^1$ is selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl, and wherein $R^2$ is independently selected from H and methyl groups; and n is an integer from 0 to 1.

8. A composition according to claim 1, wherein the composition comprises substituted cellulosic polymer comprising carboxymethyl substituent groups, and having a degree of substitution (DS) of at least 0.55, and having a degree of blockiness (DB) of at least 0.35, and having a DS+DB in the range of from 1.05 to 2.00.

9. A composition according to claim 1, wherein the composition comprises variant of *Thermomyces lanuginosa* lipase having greater than 90% identity with the wild type amino acid and comprising substitution(s) at T231 and/or N233.

10. A composition according to claim 1, wherein the composition comprises hueing agent.

11. A composition according to claim 1, wherein the composition comprises perfume microcapsule, wherein the perfume is encapsulated by a shell comprising melamine formaldehyde.

12. A composition according to claim 1, wherein the composition comprises:

(a) anionic detersive surfactant;

(b) from 0 wt % to less than 5 wt % zeolite builder;

(c) from 0 wt % to less than 5 wt % phosphate builder; and (d) optionally, from 0 wt % to 10 wt % silicate salt/

(e) from 5 to 25 wt % sodium carbonate;

(f) from 1 wt % to 10 wt % carboxylate polymer (g) variant of *Thermomyces lanuginosa* lipase having greater than 90% identity with the wild type amino acid and comprising substitution(s) at T231 and/or N233;

(h) oxaziridinium-based bleach catalyst having the formula:

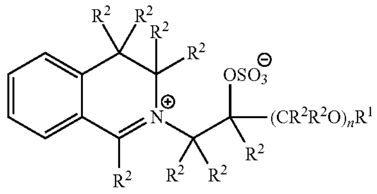

wherein $R^1$ is selected from the group consisting of: 2-propylheptyl, 2-butyloctyl, 2-pentylnonyl, 2-hexyldecyl, n-hexyl, n-octyl, n-decyl, n-dodecyl, n-tetradecyl, n-hexadecyl, n-octadecyl, iso-nonyl, iso-decyl, iso-tridecyl and iso-pentadecyl, and wherein $R^2$ is independently selected from H and methyl groups; and n is an integer from 0 to 1;

(i) optionally, co-bleach particle comprising bleach activator, source of hydrogen peroxide and optionally bleach catalyst; and (j) optionally, substituted cellulosic polymer comprising carboxymethyl substituent groups, and having a degree of substitution (DS) of at least 0.55, and having a degree of blockiness (DB) of at least 0.35, and having a DS+DB in the range of from 1.05 to 2.00.

* * * * *

SEQUENCE LISTING

```
<160> NUMBER OF SEQ ID NOS: 1

<210> SEQ ID NO 1
<211> LENGTH: 485
<212> TYPE: PRT
<213> ORGANISM: Bacillus AA560

<400> SEQUENCE: 1

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365
```

-continued

```
Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```